United States Patent [19]

Binder et al.

[11] Patent Number: 5,077,307

[45] Date of Patent: Dec. 31, 1991

[54] THIENOPYRAN DERIVATIVES, THEIR USE FOR TREATING HYPERTENSION AND ASTHMA

[75] Inventors: Dieter Binder, Vienna; Franz Rovenszky, Bruck an der Leitha; Josef Weinberger, Bad Hall; Hubert P. Ferber, Ansfelden, all of Austria

[73] Assignee: Chemisch Pharmazeutische Forschungsgesellschaft m.b.H., Linz, Austria

[21] Appl. No.: 537,629

[22] Filed: Jun. 13, 1990

[30] Foreign Application Priority Data

Jun. 27, 1989 [AT] Austria .................................. 157389

[51] Int. Cl.$^5$ .................... A61K 31/40; C07D 223/10; C07D 403/04; C07D 409/14
[52] U.S. Cl. .................................. 514/422; 514/212; 514/321; 540/531; 546/197; 548/526
[58] Field of Search ............... 540/485, 531; 546/197; 548/525, 526; 549/50; 514/212, 321, 422

[56] References Cited

FOREIGN PATENT DOCUMENTS 0076075 4/1983 European Pat. Off. .
0296795 12/1988 European Pat. Off. .

*Primary Examiner*—C. Warren Ivy
*Assistant Examiner*—Celia Chang
*Attorney, Agent, or Firm*—Wenderoth, Lind & Ponack

[57] ABSTRACT

Thienopyran derivatives of the general formula

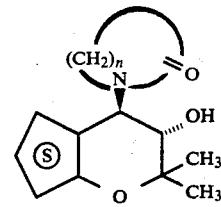

in which the radial

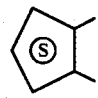

denotes one of the formulae

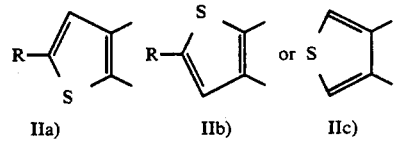

R denotes hydrogen or a radical —CN, —CHO, —CH=NOH, —CONH$_2$ or —COOR$_1$,
R$_1$ denotes the radical (C$_1$–C$_4$)-alkyl and n denotes an integer 3, 4 or 5, and a process for their preparation, pharmaceutical preparation and their use for the treatment of diseases which can be cured by activation of membrane K$^+$ channels, such as high blood pressure and asthma.

8 Claims, No Drawings

THIENOPYRAN DERIVATIVES, THEIR USE FOR TREATING HYPERTENSION AND ASTHMA

The invention relates to novel thienopyran derivatives, to a process for their preparation and to their use in medicaments for activating membrane K+ channels of the smooth musculature.

Benzopyrans which are substituted in the 4-position by N-cycloalkanones and which have hypotensive action are known from EP-A 0 076 075.

It has now been found that thienopyran derivatives have an improved pharmacological action compared to the substances of EP-A 0 076 075.

The invention therefore relates to novel thienopyran derivatives of the formula

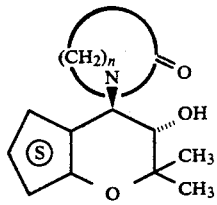

I in which the radical

denotes one of the formulae

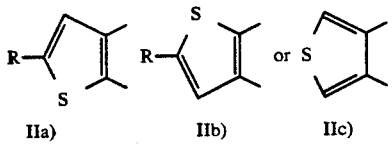

R denotes hydrogen or a radical —CN, —CHO, —CH=NOH, —CONH$_2$ or —COOR$_1$,

R$_1$ denotes the radical (C$_1$–C$_4$)-alkyl and n denotes an integer 3, 4 or 5, a process for their preparation, pharmaceutical preparations containing these compounds and their use in medicaments for the treatment of high blood pressure and asthma.

The compounds of the formula I are chiral. The present invention includes both the racemates of the compounds of the formula I and their enantiomers.

Particularly preferred individual compounds are: 6,7-dihydro-5,5-dimethyl-6-hydroxy-trans-7-(2-oxo-1-pyrrolidinyl) -5H-thieno[3,2-b]pyran-2-carbonitrile and trans-6,7-dihydro-5,5-dimethyl-6-hydroxy-7-(2-oxo-1-pyrrolidinyl) -5H-thieno[3,2-b]pyran-2-carboxamide.

The expression (C$_1$–C$_4$)-alkyl used in this description indicates straight-chain or branched saturated hydrocarbon radicals having 1 to 4 carbon atoms, such as, for example, methyl, ethyl, propyl, isopropyl, butyl, isobutyl or tert.butyl.

The compounds of the general formula I are prepared by reacting a compound of the formula

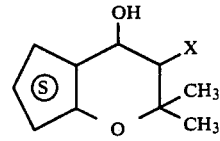

III in which the radical

denotes one of the formula

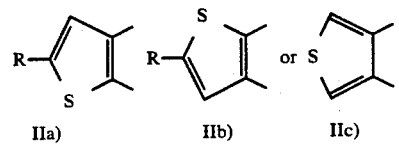

and X denotes chlorine, bromine or iodine, with a compound of the formula

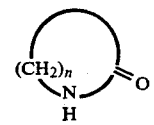

IV in which n has the meaning above, in an inert organic diluent in the presence of at least 2 equivalents of a strong, non-nucleophilic base and, if appropriate, separating the racemate thus obtained into the enantiomers.

The reaction of a compound of the formula III with a compound of the formula IV is carried out in an anhydrous organic diluent which is inert to the reaction, such as, for example, in DMF or DMSO. The amount of the diluent used is not critical in this case if an absolutely anhydrous diluent is used. If, however, even only traces of water remain in the diluent, the amount of diluent used should be kept as low as possible but on the other hand it must be observed that provision is still made for thorough mixing of the reaction components during stirring.

In order to carry out the reaction, a compound of the formula III is dissolved in the diluent and 1-3 equivalents, preferably a small excess, of a strong, non-nucleophilic base such as, for example, alkali metal hydride or alkali metal trimethylsilanolate are added with stirring. The base is in this case either dissolved in the same diluent or, in the case of the alkali metal hydride, in paraffin oil. The reaction temperature is between 0° and 40° C., room temperature being preferred. The mixture is stirred further for 5 minutes to 1 hour until epoxide formation is complete.

1-3 equivalents, preferably 1.2 to 1.6 equivalents, of a compound of the formula IV, possibly dissolved in the same diluent, and at least a further equivalent, preferably 1.2 to 1.6 equivalents, of the above base are then added successively with stirring. A larger excess of the base is not harmful; for practical reasons, however, it is attempted to keep the total amount of the base below 4 equivalents. The reaction temperature is between 0 and 50° C, preferably room temperature. The duration of the reaction is between 1 and 6 hours, the longer reaction time being associated with the lower temperatures.

After completion of the reaction, the reaction solution is neutralized or rendered weakly acidic with a weak acid, preferably with glacial acetic acid. Further working up is carried out by methods which are customary and familiar to any person skilled in the art, such as, for example, extraction, precipitation or recrystallization.

Unless enantiomerically pure starting products are used in the above reaction, a racemate is formed. This can be resolved by methods customary and familiar to a person skilled in the art, for example analogously to J. M. Evens et al., J.Med.Chem. 29, 2194 (1986). For example, a procedure is used here in which a pair of diastereomers of a urethane is produced using enantiomerically pure alpha-methylbenzyl isocyanate, these are separated by crystallization or column chromatography, and the urethane group is removed again by reduction using trichlorosilane in the presence of triethylamine.

The compounds of the general formula III can be prepared, starting from compounds of the formula V, according to the following equation and the directions in the examples according to chemical working methods which are customary and familiar to a person skilled in the art.

The compounds off the formula IV are known from the literature and commercially available.

The novel compounds of the formula I activate the membrane $K^+$ channels of the smooth musculature in in-vivo and in-vitro models.

On the basis of these pharmacological properties, the novel compounds can be used as a medicament alone or mixed with other active substances in the form of customary pharmaceutical preparations in disorders which are alleviated or cured by activation of membrane $K^{30}$ channels, such as, for example, high blood pressure or asthma.

The compounds of the formula I are intended for use in humans and can be administered in a customary manner, such as, for example, orally or parenterally. Preferably, they are administered orally, the daily dose being about 0.1 to 100 mg/kg of body weight, preferably 0.2 to 20 mg/ kg of body weight. The treating physician may, however, depending on the general condition and the age of the patient, the appropriate substance of the formula I, the nature of the disease and the type of formulation, also prescribe doses above or below this.

If the substances according to the invention are used for prophylaxis, the doses vary approximately in the same range as in the treatment case. Oral administration is also preferred in the case of prophylaxis.

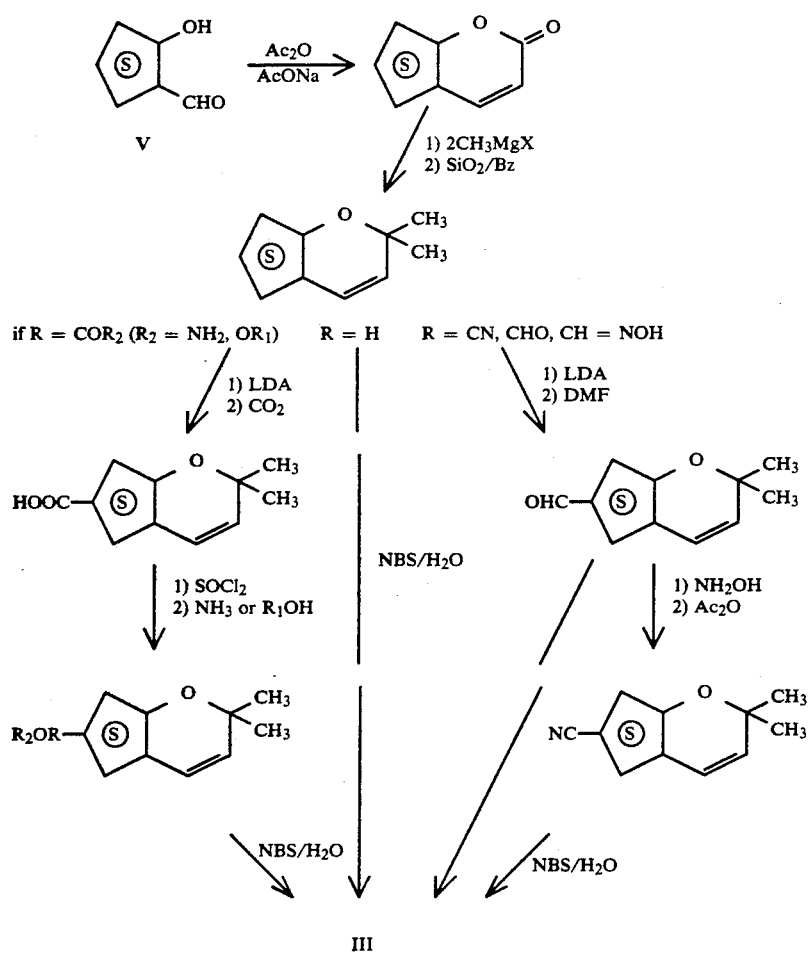

III

LDA: Lithium diisopropylamide
DMF: Dimethylformamide
NBS: N-Bromosuccinimide

The compounds of the formula I can be administered in medicaments alone or in combination with other pharmaceutically active substances, the content of the compounds of the formula I being between 0.1 and 99%. In general, the pharmaceutically active compounds are present mixed with suitable inert auxiliaries and/or excipients or diluents, such as, for example, pharmaceutically acceptable solvents, gelatin, gum arabic, lactose, starch, magnesium stearate, talc, vegetable oils, polyalkylene glycol, petroleum jelly and the like.

The pharmaceutical preparations may be present in solid form, for example as tablets, coated tablets, suppositories, capsules and the like, in liquid form, for example as solutions, suspensions or emulsions or in compositions having delayed release of the active compound. If desired, they are sterilized and contain auxiliaries, such as preservatives, stabilizers or emulsifiers, salts for altering the osmotic pressure and the like.

In particular, pharmaceutical preparations may contain the active compounds according to the invention in combination with other therapeutically useful substances. Using these, the active compounds according to the invention can be formulated to give combination preparations, for example, together with the above-mentioned auxiliaries and/or excipients.

| PE: | Petroleum ether |
|---|---|
| EA: | Ethyl acetate |
| THF: | Tetrahydrofuran |
| DMF: | Dimethylformamide |
| DMSO: | Dimethyl sulphoxide |

EXAMPLE 1 trans-6,7-Dihydro-5,5-dimethyl-6-hydroxy-7-(2-oxo-1pyrrolidinyl) -5H-thieno[3,2-b]pyran-2-carbonitrile 16.3 g (38.0 mmol) of a 26.2% strength solution of sodium trimethylsilanolate in abs. DMSO are added dropwise at room temperature to 10.2 g (35.4 mmol) of trans-6-bromo-6,7-dihydro-5,5-dimethyl-7-hydroxy-5H-thieno[3,2-b]pyran-2-carbonitrile in 50 ml of abs. DMSO. After stirring for 20 minutes, 4.3 g (50.3 mmol) of 2-pyrrolidinone and then 21.5 g (50.1 mmol) of the silanolate solution are added dropwise. After 2.5 hours, 3.7 g (62.0 mmol) of glacial acetic acid are added dropwise. The reaction mixture is partitioned between 150 ml of water and 100 ml of ethyl acetate, the phases are separated and the aqueous phase is extracted with 4×50 ml of ethyl acetate.

The combined organic phases are dried with sodium sulphate/active carbon, filtered, and the solvent is removed by distillation. 8.3 g of an orange-brown, semicrystalline material remain, which is crystallized using ethyl acetate. After filtering off and digesting with 2×15 ml of ice-cold ethyl acetate, 5.0 g of yellowish crystals remain, which are recrystallized from ethanol/active carbon.

Yield: 4.3 g of colourless crystals (41.6% of theory)
M.p.: from 233° C. dec. (ethanol)
The starting material can be prepared as follows:
5H-Thieno[3,2-b]pyran-5-one 95.0 g (0.75 mol) of 3-hydroxy-thiophene-2-carbaldehyde, 380 g (3.71 mol) of acetic anhydride and 61.0 g (0.74 mol) of anhydrous sodium acetate are heated to boiling for 88 hours. The oil bath temperature is kept at at least 170° C. during the reaction. The mixture is evaporated to dryness, and the remaining 240 g of residue are covered with 500 ml of ether and neutralized with 600 ml of saturated potassium hydrogen carbonate solution. The mixture is filtered through Hyflo and the filter cake is extracted with 5×100 ml of hot ethyl acetate. The phases are separated, and the aqueous phase is extracted with 3×200 ml of ethyl acetate. The combined organic phases are washed with 100 ml of water.

The organic solution is dried with sodium sulphate/active carbon, filtered and concentrated to give a thick magma, which is filtered and the filter cake is digested with 2×60 ml of ice-cold ethyl acetate. The remaining 74.0 g of pale brown crystals are recrystallized from acetonitrile/active carbon.

Yield: 68.2 g of pale beige crystals (60.5% of theory)
M.p.: 117°–119° C. dec. (acetonitrile)
5,5-Dimethyl-5H-thieno[3,2-b]pyran A solution of 65.0 g (0.43 mol) of 5H-thieno[3,2b]pyran-5-one in 650 ml of abs. THF is added dropwise in the course of about 35 minutes to 370 ml (1.11 mol) of 3N methylmagnesium bromide in ether such that reflux results. The mixture is subsequently stirred for 30 minutes. The reaction mixture is poured onto a mixture of 1 l of 25% strength ammonium chloride solution and 600 g of ice, the phases are separated and the aqueous phase is extracted with 3×200 ml of ether. The combined organic phases are dried with sodium sulphate/active carbon, filtered, and the solvent is removed by distillation. The remaining 98 g of red-brown oil are taken up in 600 ml of abs. benzene and heated to boiling in a water separator with 60 g of silica gel. The silica gel is filtered off, completely eluted with methanol, the filtrate is dried with sodium sulphate and filtered, and the solvent is removed by distillation. The remaining 74.5 g of brown oil are partially crystallized using 60 ml of diisopropyl ether, the crystals are filtered, the filtrate is evaporated once again and the residue (63 g) is purified by column chromatography (PE:EA=9:1, 350 g of silica gel KG 60).

Yield: 34.3 g of yellow crystals (48.3% of theory)
M.p.: 28°–32° C.
B.p.: 60°–65° C./16.0 mbar
5,5-Dimethyl-5H-thieno[3,2-b]pyran-2-carbaldehyde 96 ml (0.24 mol) of 2.5 N n-butyllithium in n-hexane are added dropwise at −40° C. to 27.0 g (0.27 mol) of diisopropylamine in 100 ml of abs. THF. 29.1 g (0.18 mol) of 5,5-dimethyl-5H-thieno[3,2-b]pyran in 300 ml of abs. THF are added to this solution at −40° C. and the mixture is kept at 0° C. for two hours. The dark red solution is reacted at −50° C. with 19.5 g (0.27 mol) of DMF in 80 ml of abs. THF. The reaction mixture is allowed to equilibrate to room temperature, is poured into 1 l of ice-water and adjusted to pH 4 with 2 N hydrochloric acid. The phases are separated, the aqueous phase is extracted with 3×100 ml of ether, the combined organic phases are washed with 100 ml of water, dried with sodium sulphate/active carbon and filtered, and the solvent is removed by distillation. The remaining 45 g of dark brown oil are purified by column chromatography (PE:EA=8:1, 200 g of KG 60).

The orange oil obtained is crystallized using diisopropyl ether, filtered and digested with 2×35 ml of ice-cold diisopropyl ether.

Yield: 23.5 g of yellow crystals (69.1% of theory)
M.p.: 58°–60° C. dec. (diisopropyl ether)
5,5-Dimethyl-5H-thieno[3,2-b]pyran-2-carbonitrile 18.45 g (95 mmol) of 5,5-dimethyl-5H-thieno[3,2b]pyran-2-carbaldehyde are added to 9.0 g (138 mmol) of hydroxylamine hydrochloride in 70 ml of abs. methanol and 7.74 g (138 mmol) of potassium hydroxide, a pH of 7 being established. After stirring at room temperature for 90 min., the solvent is stripped off at 30° C. and the residue is partitioned between 100 ml of water and 100 ml of methylene chloride. The phases are separated, the aqueous phase is extracted with 3×60 ml of methylene chloride, the combined organic phases are washed with 40 ml of water, dried with sodium sulphate and filtered, and the solvent is removed by distillation.

26.0 g of a residue remain, which is heated to boiling for 10 min in 80 ml of acetic anhydride. The solvent is stripped off in vacuo and the residue is covered with 70 ml of ether. The suspension is neutralized with sodium carbonate solution and filtered through Hyflo. The phases are separated, the aqueous phase is extracted with 3×30 ml of ether, the combined organic phases are washed with sodium carbonate solution, dried with sodium sulphate/active carbon and filtered, and the solvent is removed by distillation.

Yield: 13.2 g of orange-brown crystals (72.5% of theory)

M.p.: 73°-75° C. (petroleum ether)

trans-6-Bromo-6,7-dihydro-5,5-dimethyl-7-hydroxy-5Hthieno [3,2-b]pyran-2-carbonitrile 2.1 g (117 mmol) of water and 20.5 g (115 mmol) of N-bromosuccinimide are added to 11.0 g (57.5 mmol) of 5,5-dimethyl-5H-thieno[3,2-b]pyran-2-carbonitrile in 100 ml of abs. DMSO.

After stirring for 20 min., the reaction mixture is partitioned between 250 ml of water and 150 ml of ethyl acetate and the aqueous phase is saturated with sodium chloride. The phases are separated. The aqueous phase is extracted with 3×50 ml of ethyl acetate. The combined organic phases are washed with 2×70 ml of saturated potassium hydrogen carbonate solution and 50 ml of water. The organic solution is dried with sodium sulphate/active carbon and filtered, and the solvent is removed by distillation. The remaining 18.0 g of pale yellow crystals are recrystallized from methanol using active carbon.

Yield: 14.2 g of colourless crystals (85.7% of theory)

M.p.: 155.5°-156.0° C. dec. (methanol)

EXAMPLE 2 trans-6,7-Dihydro-5,5-dimethyl-6-hydroxy-7-(2-oxo-1pyrrolidinyl) -5H-thieno[3,2-b]pyran-2-carboxamide 0.32 g (7.29 mmol) of 55% strength sodium hydride dispersion in paraffin oil are added to 2.0 g (6.9 mmol) of trans-6-bromo-6,7-dihydro-5,5-dimethyl-7-hydroxy-5Hthieno[3,2-b]pyran-2-carbonitrile in 10 ml of abs. DMSO at room temperature. After 70 min, 0.85 g (10.0 mmol) of 2-pyrrolidinone and then 0.44 g (10.0 mmol) of sodium hydride dispersion are added. The reaction mixture is diluted dropwise with 25 ml of water and 0.5 ml of glacial acetic acid after 45 min, and the precipitated crystals are filtered and digested with 2 x 5 ml of ice-cold petroleum ether. The beige crystals obtained are recrystallized from methanol/dimethylformamide.

Yield: 0.92 g of colourless crystals (42% of theory)

M.p.: 297° C. dec. (methanol/DMF)

EXAMPLE 3

Racemate resolution

The racemate resolution scheme is shown in the following equation:

Racemate resolution equation

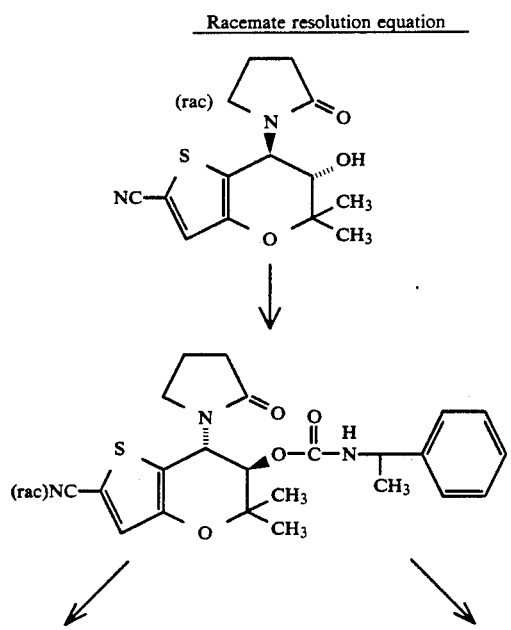

-continued
Racemate resolution equation

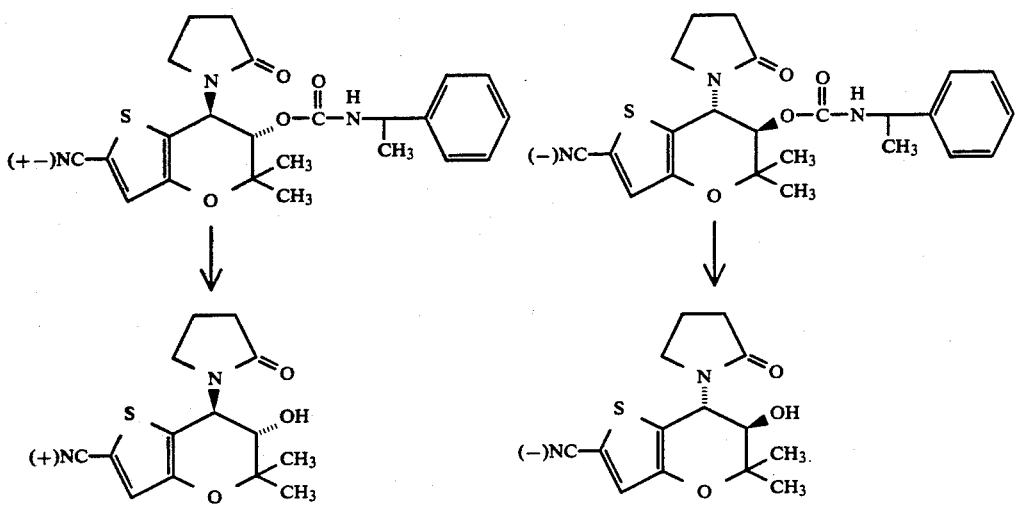

1. Reaction to give rac-2-cyano-6,7-dihydro-7-(2-oxo-1pyrrolidinyl) -N-[(1-phenyl)-ethyl]-5H-thieno[3,2-b]pyran-6-carbamate 4.5 g (15.4 mmol) of rac-6,7-dihydro-5,5-dimethyl-6-hydroxy-7-(2-oxo-1-pyrrolidinyl)-5H-thieno[3,2-b]pyran-2-carbonitrile are suspended in toluene with 2.49 g (16.9 mmol of (S)-(-)-alpha-methylbenzyl isocyanate and the mixture is heated to boiling. The reaction is complete after 70 hours and the solution, which is now clear, is evaporated to dryness.

The remaining 6.85 g of yellowish crystals are recrystallized from acetone and active carbon. Yield: 5.31 g of colourless crystals (78.5% of theory) M.p.: 203°–207° C. (acetone)

2. Separation of the diastereomers

The separation is carried out by column chromatography, the mixed fractions obtained in each case being separated again. Eluent $CHCl_3:Et_2O = 5:1$ Stationary phase: 300 g of silica gel KG 60 Starting quantity: 5.3 g of diastereomer mixture Result from 3 separations:

TABLE 1

|  | First | Second | Third | Fourth |
|---|---|---|---|---|
|  | Separation |  |  |  |
| 1st fraction | 0.82 g | 0.68 g | 0.29 g | 1.79 g |
| Mixed fraction | 3.80 g | 2.35 g | 1.61 g | 1.61 g |
| 2nd fraction | 0.52 g | 0.56 g | 0.59 g | 1.67 g | a) 1st fraction:

(+)-2-Cyano-6,7-dihydro-7-(2-oxo-1-pyrrolidinyl)-N-[(1-phenyl)-ethyl]-5H-thieno[3,2-b]pyran-6-carbamate M.p.: 198°–200° C. (acetone) $c_1$ (acetone) $-0.52°$ b) 2nd fraction:

(−)-2-Cyano-6,7-dihydro-7-(2-oxo-1-pyrrolidinyl)-N-[(1-phenyl)-ethyl]-5H-thieno[3,2-b]pyran-6-carbamate M.p.: 203°–205° C. (acetone) $c_1$ (acetone) $-0.44°$ 3. Removal of the auxiliary group In each case 1.4 g (3.2 mmol) of the separated diastereomer is dissolved in 12 ml of toluene containing 0.65 g (6.4 mmol) of triethylamine under a nitrogen atmosphere. 0.87 g (6.4 mmol) of trichlorosilane is added dropwise at 40° C. and the mixture is stirred at this temperature for 3 hours. It is subsequently stirred overnight at room temperature.

1.5 ml of methanol are added to the reaction mixture and the mixture is held at 80° C. for 15 min and allowed to cool, and the precipitated ammonium chloride is filtered off.

After stripping off the solvent, the crude product is subjected to a chromatographic purification (70 g of silica gel KG 60, eluent: ethyl acetate).

The product obtained is recrystallized from ethanol again.

a) (+)-trans-6,7-Dihydro-5,5-dimethyl-6-hydroxy-7-(2-oxo-1-pyrrolidinyl) -5H-thieno[3,2-b]pyran-2-carbonitrile Yield: 0.66 g of colourless crystals (71.0% of theory) $c_1$ (methanol) $+0.93°$ M.p.: 187° C. dec. (ethanol)

b) (-)-trans-6,7-Dihydro-5,5-dimethyl-6-hydroxy-7-(2-oxo1-pyrrolidinyl) -5H-thieno[3,2-b]pyran-2-carbonitrile Yield: 0.74 g of colourless crystals (79.6% of theory) $c_1$ (methanol) $-0.91°$ M.p.: 189° C. dec. (ethanol)

EXAMPLE 4

Actions of the substance of Example 1 on the blood pressure of the conscious, spontaneously hypertensive rat.

The investigations were carried out on spontaneously hypertensive rats (Madörin, Switzerland, 245–395 g). The experimental animals had a catheter permanently tied into the carotid artery, which was connected to a transducer (Statham) for blood pressure measurement. The data were prepared in a Hellige cardiovascular analyzer and recorded on a Watanabe WR 3101-4 recorder.

The compound of Example 1 was dissolved in a 10% strength alcoholic solution and administered, either intravenously into the tail vein or orally. The solvent without test substance was administered as a control. The actions on the blood pressure were recorded for up to one hour after i.v. administration and for up to 3 hours after oral administration of the substance.

4–5 experiments were carried out per concentration. The $ED_{20}$ (the value which reduces the diastolic blood pressure by 20%) was calculated by linear regression analysis from the values thus obtained.

The results are summarized in Table 2.

TABLE 2

| Concentration (mcg/kg) | Change in the systolic blood pressure in % | Change in the diastolic blood pressure in % |
|---|---|---|
| 0 (control) | −1.8% (±2,5) | −1.5% (±4.4) |
| 10 (i.v.) | −9.2% (±3.4) | −5.6% (±7.3) |
| 30 (i.v.) | −30.0% (±4.8) | −46.0% (±6.0) |
| 100 (i.v.) | −41.0% (±6.6) | −65.5% (±3.7) |
| 30 (p.o.) | −2.3% (±2.5) | −4.5% (±2.9) |
| 100 (p.o.) | −26.5% (±5.4) | −23.0% (±6.7) |
| 300 (p.o.) | −38.0% (±12.2) | −36.8% (±13.1) |

An $ED_{20}$ i.v. of 15.5 mcg/kg and an $ED_{20}$ p.o. of 90.4 mcg/kg were calculated from these values.

EXAMPLE 5

Example 4 was repeated with the exception that cromakalim (3,4-dihydro-2,2-dimethyl-3-hydroxy-trans-4-(2-oxo-1-pyrrolidinyl) -2H-benzo[b]pyran-6-carbonitrile, the preferred substance of EP-A 0,076,075) was used as the test substance. The results of these experiments are summarized in Table 3.

TABLE 3

| Concentration (mcg/kg) | Change in the systolic blood pressure in % | Change in the diastolic blood pressure in % |
|---|---|---|
| 0 (control) | −1.8% (±2,5) | −1.5% (±4.4) |
| 10 (i.v.) | −6.6% (±4.0) | −6.6% (±6.3) |
| 30 (i.v.) | −26.5% (±5.9) | −27.5% (±7.9) |
| 100 (i.v.) | −36.3% (±9.0) | −58.3% (±7.9) |
| 30 (p.o.) | −3.3% (±1.0) | −4.3% (±1.5) |
| 100 (p.o.) | −11.5% (±6.8) | −11.3% (±9.2) |
| 300 (p.o.) | −22.8% (±10.8) | −24.5% (±11.3) |

An $ED_{20}$ i.v. of 19.4 mcg/kg and an $ED_{20}$ p.o. of 213.4 mcg/kg result from these values.

What is claimed is:

1. A compound of the formula

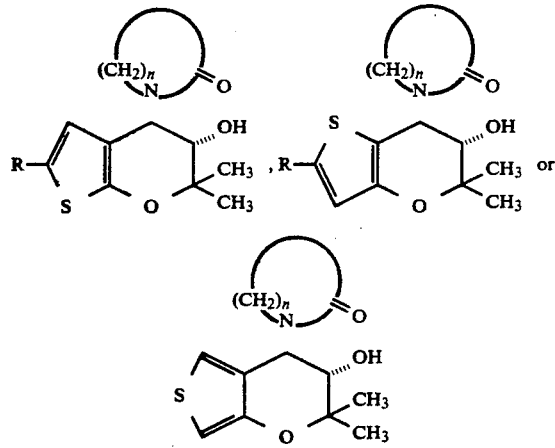

wherein:
R denotes hydrogen, —CN, —CHO, —CH=NOH, —CONH₂ or —COOR₁,
R₁ denotes (C₁-C₄)-Alkyl and n denotes an integer 3, 4 or 5.

2. (±) Trans-6,7-dihydro-5,5-dimethyl-6-hydroxy-7-(2-oxo-1-pyrrolidinyl)-5H-thieno [3,2-b]pyran-2-carbonitrile.

3. (±) Trans-6,7-dihydro-5,5-dimethyl-6-hydroxy-7-(2-oxo-1-pyrrolidinyl) -5H-thieno[3,2-b]pyran-2-carboxamide.

4. The compound according to claim 1 in enantiomerically pure form.

5. The compound according to claim 1 in mixtures of the optical antipodes.

6. (−)-Trans-6,7-dihydro-5,5-dimethyl-6-hydroxy-7(2-oxo-1-pyrrolidinyl) -5H-thieno(3,2-b)pyran-2-carbonitrile.

7. A pharmaceutical composition comprising a compound of the formula

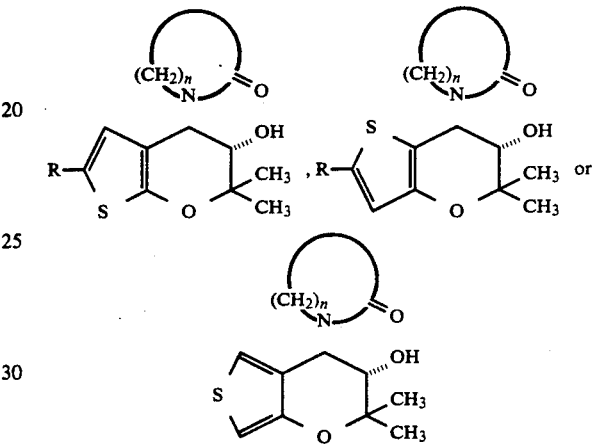

wherein R denotes hydrogen, —CN, —CHO, —CH=NOH, —CONH₂ or COOR₁, wherein R₁ denotes (C₁-C₄) alkyl and
n denotes an integer 3, 4, or 5,
in an amount effective for the treatment of high blood pressure or asthma in combination with pharmaceutically acceptable excipients, carrier or diluents.

8. A method for the treatment of high blood pressure or asthma which comprises administering an effective amount for the treatment of high blood pressure or asthma of a compound of the formula

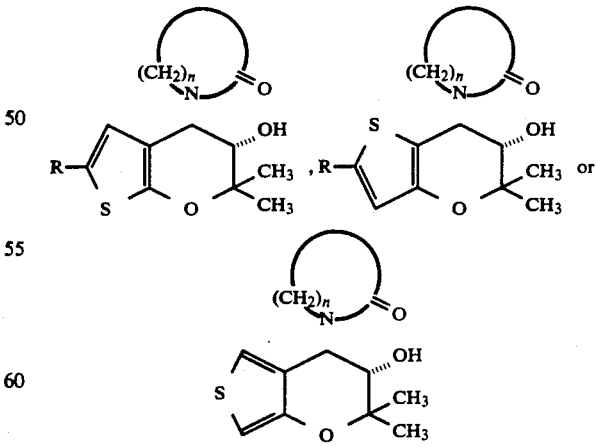

wherein R denotes hydrogen, —CN, —CHO —CH=NOH, —CONH₂ or COOR₁, where R₁ denotes (C₁-C₄) alkyl and
n denotes an integer 3, 4 or 5.

* * * * *

UNITED STATES PATENT AND TRADEMARK OFFICE
CERTIFICATE OF CORRECTION

PATENT NO. : 5,077,307                                    Page 1 of 2

DATED      : December 31, 1991

INVENTOR(S): Dieter Binder et al

It is certified that error appears in the above-indentified patent and that said Letters Patent is hereby corrected as shown below:

In Column 4, line 10, change "$K30$" to --$K^+$--.

IN THE CLAIMS

Claim 1, line 1 (counting the formulae as one line),
Claim 7, line 3 (counting the formulae as one line),
Claim 8, line 5 (counting the formulae as one line), change

UNITED STATES PATENT AND TRADEMARK OFFICE
CERTIFICATE OF CORRECTION

PATENT NO. : 5,077,307

DATED : December 31, 1991

INVENTOR(S) : Dieter Binder et al

It is certified that error appears in the above-indentified patent and that said Letters Patent is hereby corrected as shown below:

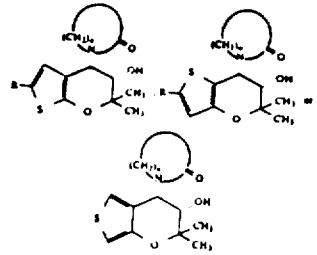

to --

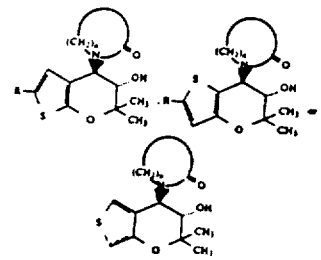

--.

Signed and Sealed this

First Day of March, 1994

Attest:

BRUCE LEHMAN

Attesting Officer     Commissioner of Patents and Trademarks